(12) United States Patent
Tsou et al.

(10) Patent No.: US 9,723,979 B2
(45) Date of Patent: Aug. 8, 2017

(54) METHOD, APPARATUS AND COMPUTER PROGRAM PRODUCT FOR POSITIONING PUPIL

(71) Applicant: UTECHZONE CO., LTD., New Taipei (TW)

(72) Inventors: Chia-Chun Tsou, New Taipei (TW); Po-Tsung Lin, New Taipei (TW)

(73) Assignee: UTECHZONE CO., LTD., New Taipei (TW)

( * ) Notice: Subject to any disclaimer, the term of this patent is extended or adjusted under 35 U.S.C. 154(b) by 93 days.

(21) Appl. No.: 14/521,477

(22) Filed: Oct. 23, 2014

(65) Prior Publication Data
US 2016/0045109 A1   Feb. 18, 2016

(30) Foreign Application Priority Data
Aug. 14, 2014   (TW) .............................. 103127951 A

(51) Int. Cl.
| | | |
|---|---|---|
| *A61B 3/14* | (2006.01) | |
| *A61B 3/113* | (2006.01) | |
| *A61B 3/00* | (2006.01) | |
| *G06F 3/01* | (2006.01) | |
| *G06K 9/00* | (2006.01) | |
| *G06T 7/60* | (2017.01) | |
| *G06T 7/73* | (2017.01) | |

(52) U.S. Cl.
CPC ............ *A61B 3/113* (2013.01); *A61B 3/0025* (2013.01); *G06F 3/013* (2013.01); *G06K 9/0061* (2013.01); *G06T 7/60* (2013.01); *G06T 7/75* (2017.01); *A61B 3/145* (2013.01); *G06T 2207/30201* (2013.01)

(58) Field of Classification Search
CPC ........... A61B 3/152; A61B 3/145; A61B 3/14; A61B 3/12; A61B 3/103; A61B 3/1015
USPC ................................. 351/204–206, 208, 246
See application file for complete search history.

(56) References Cited

U.S. PATENT DOCUMENTS

| | | | |
|---|---|---|---|
| 5,499,303 A | 3/1996 | Hundt et al. | |
| 5,912,721 A * | 6/1999 | Yamaguchi et al. | .......... 351/210 |
| 7,948,493 B2 | 5/2011 | Klefenz et al. | |

FOREIGN PATENT DOCUMENTS

| | | |
|---|---|---|
| CN | 101964111 | 2/2011 |
| CN | 102149325 | 1/2013 |
| JP | H08145644 | 6/1996 |
| TW | 201127451 | 8/2011 |
| WO | 2008007781 | 1/2008 |

OTHER PUBLICATIONS

"Office Action of Taiwan Counterpart Application", issued on Mar. 17, 2016, p. 1-p. 10.
"Office Action of Taiwan Counterpart Application", issued on Nov. 6, 2015, p. 1-p. 10.

(Continued)

*Primary Examiner* — James Greece
(74) *Attorney, Agent, or Firm* — Jianq Chyun IP Office

(57) ABSTRACT

A method, an apparatus and a computer program product for positioning pupil are provided. A pupil contour is obtained from a pupil image after the pupil image is obtained. And an ellipse feature is obtained according to curvature information of the pupil contour, and then a sight direction is determined according to the ellipse feature.

15 Claims, 4 Drawing Sheets

(56) References Cited

OTHER PUBLICATIONS

Xia et al., "IR Image Based Eye Gaze Estimation", Software Engineering, Artificial Intelligence, Networking, and Parallel/Distributed Computing, Jul. 30-Aug. 1, 2007, pp. 220-224.
"Office Action of Taiwan Counterpart Application", issued on Jan. 4, 2016, p. 1-p. 10.
Keniji Mastuda, et al., "A System for Measuring Eye Position," Technical report of IEICE, TL2000-2, The Institute of Electronics, Information and Communication Engineers, vol. 1, No. 47, May 2000, pp. 9-16.
"Office Action of Japan Counterpart Application," issued on Jun. 14, 2016, p. 1-p. 5.
"Office Action of Taiwan Counterpart Application", issued on Jun. 1, 2016, p. 1-p. 10.

\* cited by examiner

METHOD, APPARATUS AND COMPUTER PROGRAM PRODUCT FOR POSITIONING PUPIL

CROSS-REFERENCE TO RELATED APPLICATION

This application claims the priority benefit of Taiwan application serial no. 103127951, filed on Aug. 14, 2014. The entirety of the above-mentioned patent application is hereby incorporated by reference herein and made a part of this specification.

BACKGROUND

Technical Field

The invention relates to a visual recognition technique, and particularly relates to a method, an apparatus and a computer program product for positioning pupil.

Related Art

A current eye tracking technique is mainly divided into an invasive eye tracking technique and a non-invasive eye tracking technique. The invasive eye tracking technique is to set a search coil in the eye or to use an electrooculogram. The non-invasive eye tracking technique includes a free-head eye tracking technique or a head-mount eye tracking technique. Along with development of technology, the eye tracking technique is widely applied in various domains such as neuroscience, psychology, industrial engineering, human factors engineering, marketing advertising, computer science, etc.

By using the eye tracking technique to assist communication of speaking inconveniences and physical difficulties, it brings many conveniences to person with restricted mobility. For example, with assistance of eye movement electronic products, the eyes can be used to replace a mouse to implement communication, Internet access, video-audio entertainment activities, etc. However, since the invasive and non-invasive eye tracking techniques have to be used in collaboration with expensive software and hardware equipment, and require a complicated calibration procedure, stability of execution state thereof is poor, and the product cost is relatively high, such that the eye tracking technique cannot be popularised.

SUMMARY

The invention is directed to a method, an apparatus and a computer program product for positioning pupil, by which a location of the pupil is accurately positioned, so as to achieve accurate eye tracking.

The invention provides a method for positioning pupil, which includes following steps. A pupil image is obtained. A pupil contour is obtained from the pupil image. An ellipse feature is obtained according to curvature information of the pupil contour. A sight direction is determined according to the ellipse feature.

In an embodiment of the invention, the curvature information includes curvatures of one or a plurality of curve segments. The step of obtaining the ellipse feature according to the curvature information of the pupil contour includes following steps. Curvatures of a plurality curves of the pupil contour are calculated from a start point of the pupil contour along a predetermined direction. In an error tolerance range, it is determined whether the curvature of each curve is complied with a same curvature equation. A plurality of continuous curves complied with the same curvature equation within the error tolerance range are set as a same curve segment. The ellipse feature is obtained according to the one or more curve segments obtained based on the pupil contour.

In an embodiment of the invention, the step of obtaining the ellipse feature according to the curvature information of the pupil contour further includes filtering the one or more curve segments that are not complied with a predetermined curving direction.

In an embodiment of the invention, the step of determining the sight direction according to the ellipse feature includes inquiring the sight direction corresponding to the ellipse feature from a database.

In an embodiment of the invention, the method for positioning pupil further includes calculating a pupil displacement, so as to obtain a displacement of a sight point.

In an embodiment of the invention, the method for positioning pupil further includes following steps. An original image is received. A face image is extracted from the original image. A nostril area of the face image is detected to obtain nostril position information. An eye image is obtained based on the nostril position information, and the pupil image is obtained from the eye image.

In an embodiment of the invention, the step of obtaining the eye image according to the nostril location information includes following steps. A central point and a length and a width of an eye search frame are estimated according to a distance between a first nostril central point and a second nostril central point in the nostril position information, so as to obtain the eye image from the eye search frame.

The invention provides a pupil positioning apparatus including an image capturing unit, a storage unit and a processing unit. The image capturing unit is configured to obtain an original image. The storage unit includes an image analysis module. The processing unit is coupled to the image capturing unit and the storage unit. The processing unit activates the image analysis module to obtain a pupil image from the original image, obtain a pupil contour from the pupil image, obtain an ellipse feature according to curvature information of the pupil contour, and determine a sight direction according to the ellipse feature.

The invention provides a computer program product, which is adapted to a pupil positioning apparatus, and when the pupil positioning apparatus loads and executes a computer program of the computer program product, the aforementioned method for positioning pupil is implemented.

According to the above descriptions, the sight direction of the pupil and the pupil displacement can be quickly and accurately detected, so as to implement accurate eye tracking to achieve diversified application.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

A general eye tracking technique is to use a light source to irradiate user's eye, so as to form a light spot on a surface of the eye, and a sight direction of the user is determined according to a relative position between a pupil and the light spot. However, a calibration procedure has to be performed before the conventional method is used, so as to avoid an error in conversion of a screen position. Therefore, the invention provides a method, an apparatus and a computer program product for positioning pupil, by which a curvature of the pupil is used as a feature to implement eye movement control.

Figure 1:
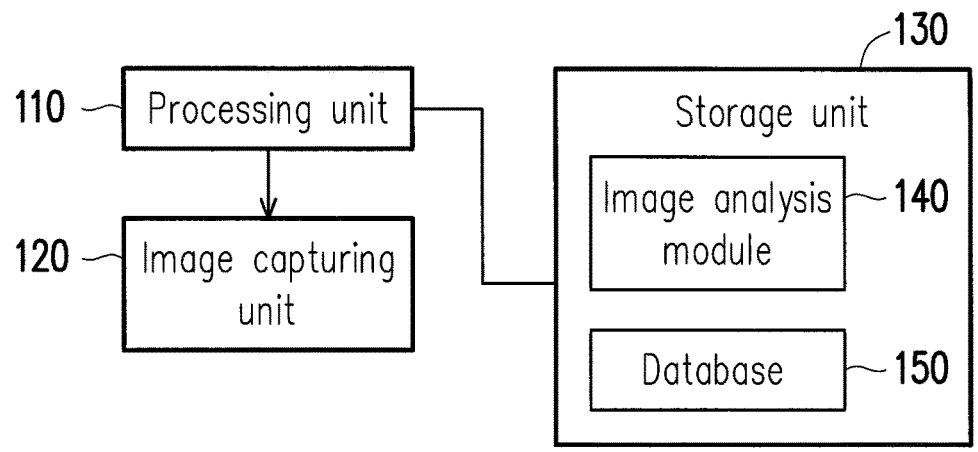
FIG. 1 is a block diagram of a pupil positioning apparatus according to an embodiment of the invention.

FIG. 1 is a block diagram of a pupil positioning apparatus according to an embodiment of the invention. The pupil positioning apparatus 100 is used to convert a pupil position of a user into a cursor position on a screen. The pupil positioning apparatus 100 may have an inbuilt screen, or can be connected to a screen. The pupil positioning apparatus 100 is, for example, an electronic apparatus or an electronic product having a computing capability such as a desktop computer, a notebook, a tablet personal computer, a smart phone, etc.

Referring to FIG. 1, the pupil positioning apparatus 100 mainly includes a processing unit 110, an image capturing unit 120 and a storage unit 130. The processing unit 110 is, for example, a central processing unit (CPU), or a programmable general purpose or special purpose microprocessor, a digital signal processor (DSP), a programmable controller, an application specific integrated circuits (ASIC), a programmable logic device (PLD) or other similar devices or a combination of the devices.

The image capturing unit 120 is, for example, a video camera or a camera, which has a charge coupled device (CCD) lens, a complementary metal oxide semiconductor transistor (CMOS) lens, or an infrared lens. The image capturing unit 120 is used for capturing an image sequence (including a plurality of original images).

The storage unit 130 is, for example, a fixed or removable random access memory (RAM) of any type, a read-only memory (ROM), a flash memory, a hard disc or other similar devices or a combination of the devices.

In the present embodiment, program instructions are used to implement positioning of the pupil, i.e. the storage unit 130 stores a plurality of program instructions, and after the program instructions are loaded, the processing unit 110 executes the program instructions. For example, the storage unit 130 includes an image analysis module 140 composed of one or a plurality of program instructions, and the image analysis module 140 is used to execute a plurality of functions. Moreover, the storage unit 130 further includes a database 150. The database 150 stores a plurality of predetermined ellipse features and corresponding sight directions.

When a three-dimensional (3D) eyeball is converted into a two-dimensional (2D) image, the pupil in the 2D image has some curvature deformation, therefore, the sight direction can be determined by analysing curvature information. In detail, the processing unit 110 activates the image analysis module 140 to obtain a pupil image from the original image, obtain a pupil contour from the pupil image, obtain an ellipse feature according to curvature information of the pupil contour, and determine the sight direction according to the ellipse feature. For example, the image analysis module 140 inquires the database 150 to obtain the corresponding sight direction according to the predetermined ellipse feature complying with the ellipse feature. The ellipse feature is, for example, an ellipse equation.

Figure 2:
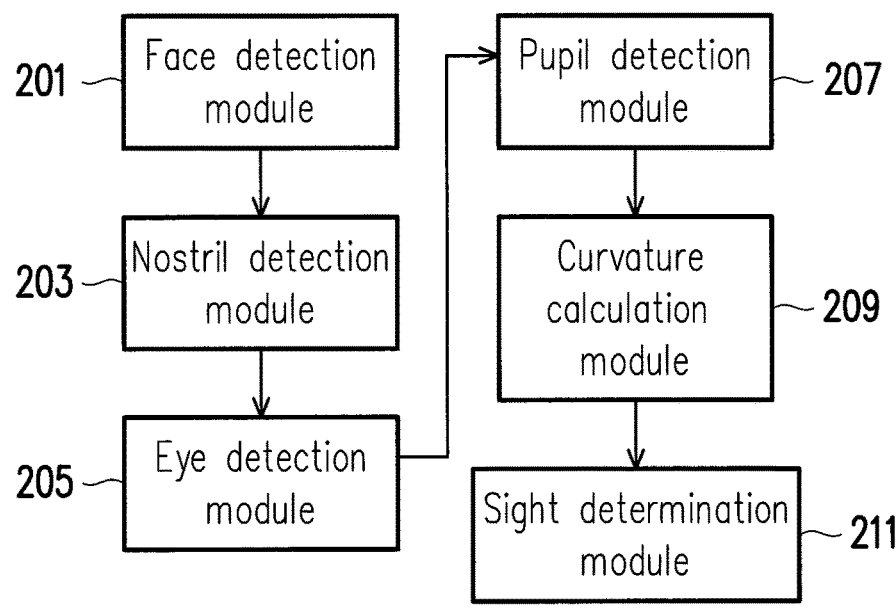
FIG. 2 is a block diagram of an image analysis module according to an embodiment of the invention.

The image analysis module 140 is described below. FIG. 2 is a block diagram of the image analysis module according to an embodiment of the invention. The image analysis module 140 includes a face detection module 201, a nostril detection module 203, an eye detection module 205, a pupil detection module 207, a curvature calculation module 209 and a sight determination module 211. The face detection module 201 is configured to extract a face image from the original image. The nostril detection module 203 is configured to detect a nostril area of the face image to obtain nostril position information. The eye detection module 205 is configured to obtain an eye image according to the nostril position information. The pupil detection module 207 is configured to detect a pupil image from the eye image, and obtain a pupil contour from the pupil image. The curvature calculation module 209 is configured to calculate curvature information of the pupil contour to obtain an ellipse feature. The sight determination module 211 is configured to determine a sight direction according to the ellipse feature.

Figure 3:
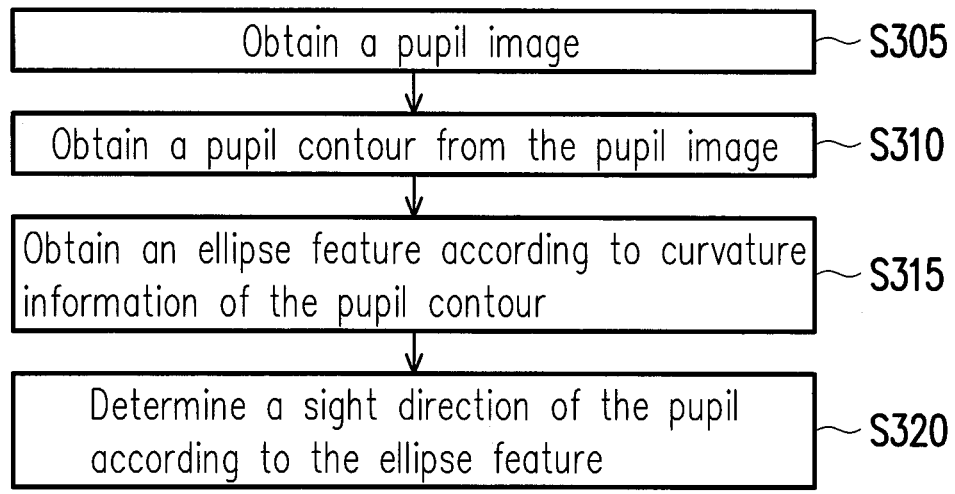
FIG. 3 is a flowchart illustrating a method for positioning pupil according to an embodiment of the invention.

The method for positioning pupil is described with reference of the aforementioned pupil positioning apparatus 100. FIG. 3 is a flowchart illustrating a method for positioning pupil according to an embodiment of the invention. First, in step S305, the image analysis module 140 obtains a pupil image. For example, after the image capturing unit 120 receives an original image, the processing unit 110 activates the image analysis module 140 to obtain a face image from the original image first, detect a nostril area of the face image to obtain nostril position information, and obtain an eye image according to the nostril position information. Thereafter, the processing unit 110 obtains the pupil image from the eye image according to a pupil detecting algorithm.

Taking the image analysis module 140 of FIG. 2 as an example, the face detection module 201 detects whether the original image captured by the image capturing unit 120 has a face object according to a face recognition algorithm, and obtains the face image from the original image. For example, the storage unit 130 stores a feature database. The feature database includes a plurality of face feature patterns. The face detection module 201 obtains the face object by comparing the face feature patterns in the feature database. In an exemplary embodiment, an AdaBoost algorithm based on Haar-like feature or other existing face recognition algorithms can be used to obtain the face image in the original image.

Then, the nostril detection module 203 receives the face image from the face detection module 201, and detects the nostril area of the face image to obtain the nostril position information. Since the nostrils in human face present a black color, it is easy to be correctly recognized. Therefore, in the present embodiment, the feature of the nostrils is used to obtain other features on the face. The nostril position information is, for example, a first nostril central point and a second nostril central point of the two nostrils.

Since general facial feature proportions have approximate value ranges in statistics, according to a statistic facial feature proportion relationship, after the nostril position information is obtained, the eye detection module 205 can obtain an eye area position according to the nostril position information. For example, the eye detection module 205 estimates a central point and a length and a width of an eye search frame according to a central point of a connection line between the first nostril central point and the second nostril central point in the nostril position information, so as to obtain the eye image from the eye search frame.

Figure 4:
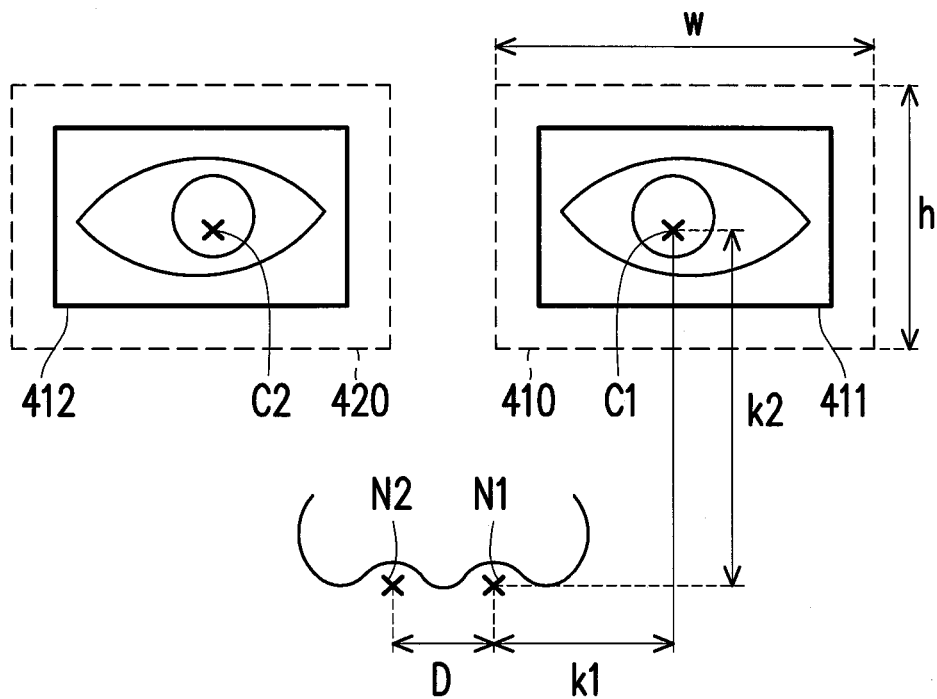
FIG. 4 is a schematic diagram of estimating an eye search frame according to an embodiment of the invention.

For example, FIG. 4 is a schematic diagram of estimating an eye search frame according to an embodiment of the invention. After a first nostril central point N1 and a second nostril central point N2 are found, a distance D between the first nostril central point N1 and the second nostril central point N2 is calculated. Then, a central point and a length and a width of the eye search frame of each eye are estimated according to the distance D. In detail, taking the first nostril central point N1 with coordinates of (N1_x, N1_y) as a start point, the X-coordinate is added by a first estimate value k1, and the Y-coordinate is added by a second estimate value k2 to obtain a central point C1, i.e. the X-coordinate of the central point C1 is C_x=N1_x+k1, and the Y-coordinate thereof is C_y=N1_y+k2. Setting of the first and the second estimate values k1 and k2 can be: k1=D×e1, k2=D×e2, where 1.3<e1<2.0, and 1.5<e2<2.2, which can be adjusted according to an actual requirement, and are not limited by the invention. After the central point C1 is obtained, an eye search frame 410 is obtained according to predefined width w and height h, where the width w is greater than the height h. For example, the width w is 2×22 pixels, and the height h is 2×42 pixels.

Further, similar to the above method, taking the second nostril central point N2 with coordinates of (N2_x, N2_y) as a start point, the first estimate value k1 is subtracted from the X-coordinate, and the Y-coordinate is added by the second estimate value k2 to obtain another central point C2. After the central point C2 is obtained, another eye search frame 420 is obtained according to predefined width w and height h. Moreover, in other embodiments, the start point can also be the central point between the first nostril central point N1 and the second nostril central point N2, which is not limited by the invention. After the eye searching frames 410 and 420 are obtained, the processing unit 110 further obtains more accurate eye images 411 and 421 from the eye search frames 410 and 420.

Thereafter, the eye detection module 205 adjusts a contrast of the eye images 411 and 421 to obtain enhanced images, performs a de-noise processing on the enhanced images to obtain de-noised images, performs an edge sharpening processing on the de-noised images to obtain sharpened images, and performs a binarization processing on the sharpened images to obtain binarized images. Thereafter, the eye detection module 205 again performs the edge sharpening processing on the binarized images to obtain eye objects. Then, the pupil detection module 207 respectively executes a pupil detecting algorithm on the eye objects to obtain the pupil images.

However, the above implementation of obtaining the pupil image is only an example, and the invention is not limited thereto. For example, the image analysis module 140 can also directly obtain the eye image by using eye features, and the step of obtaining the nostril position information can be omitted.

Figure 5A:
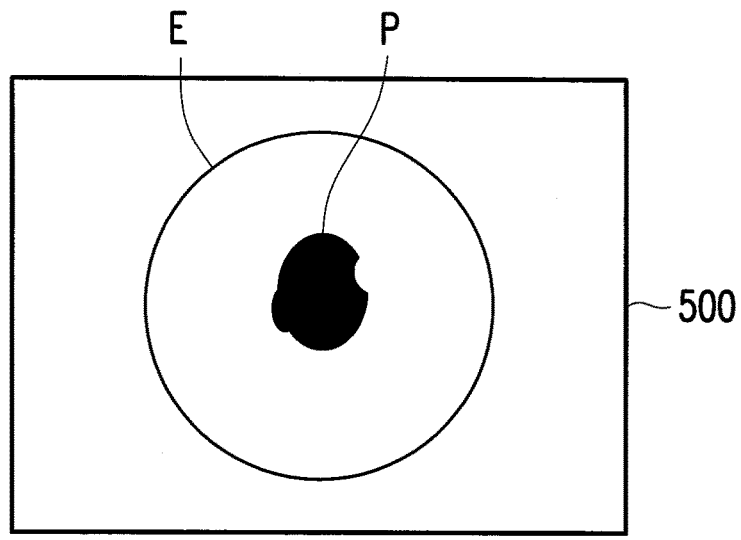
FIG. 5A is a schematic diagram of a pupil image according to an embodiment of the invention.
Figure 5B:
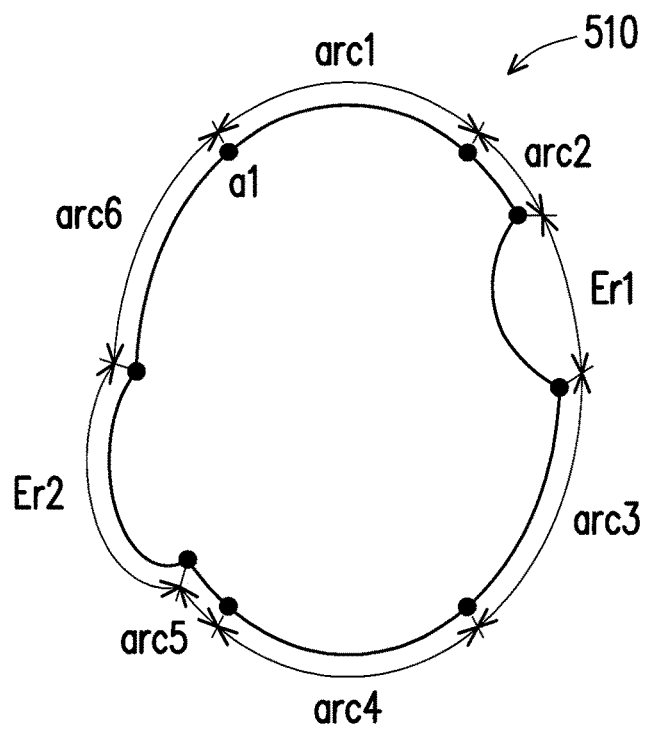
FIG. 5B is a schematic diagram of a pupil contour according to an embodiment of the invention.

Referring back to FIG. 3, in step S310, the image analysis module 140 obtains pupil contours from the pupil images. For example, FIG. 5A is a schematic diagram of a pupil image according to an embodiment of the invention, FIG. 5B is a schematic diagram of a pupil contour according to an embodiment of the invention. Referring to FIG. 5A and FIG. 5B, the pupil detection module 207 detects that the pupil image 500 includes an eye object E and a pupil object P. Then, the pupil detection module 207 executes an edge detecting algorithm to the pupil object P to obtain the pupil contour 510 shown in FIG. 5B.

After the pupil contour 510 is obtained, in step S315, the image analysis module 140 obtains an ellipse feature according to curvature information of the pupil contour 510. In detail, the curvature calculation module 209 calculates curvatures of one or a plurality of curve segments included in the pupil contour 510. The curvature information includes the curvatures in the curve segments. In the present embodiment, the pupil contour 510 shown in FIG. 5B includes a plurality of curve segments. Moreover, in other embodiments, in case that the pupil contour 510 has a round shape, the pupil contour 510 only includes one curve segment.

The curvature calculation module 209 calculates curvatures of a plurality curves in the pupil contour 510 from a start point a1 of the pupil contour 510 along a predetermined direction (a clockwise direction in the present embodiment). In an error tolerance range, a least square error (LSE) algorithm, a modified mild-slope equation (MMSE) algorithm, a neural network algorithm, or a genetic algorithm, etc. is used to determine whether the curvatures of the curves are complied with a curvature equation. Moreover, the curves complied with the same curvature equation within the error tolerance range are set as a same curve segment. Taking FIG. 5B as an example, the pupil contour 510 may include curve segments arc1-arc6 and curve segments Er1-Er2. Moreover, the curvature calculation module 209 further filters the curve segments Er1-Er2 that are not complied with a predetermined curving direction (concave, convex). Thereafter, the curvature calculation module 209 obtains the ellipse feature (for example, an ellipse equation) according to the curve segments arc1-arc6 obtained from the pupil contour 510. A corresponding ellipse shape can be obtained according to the ellipse feature.

Figure 6:
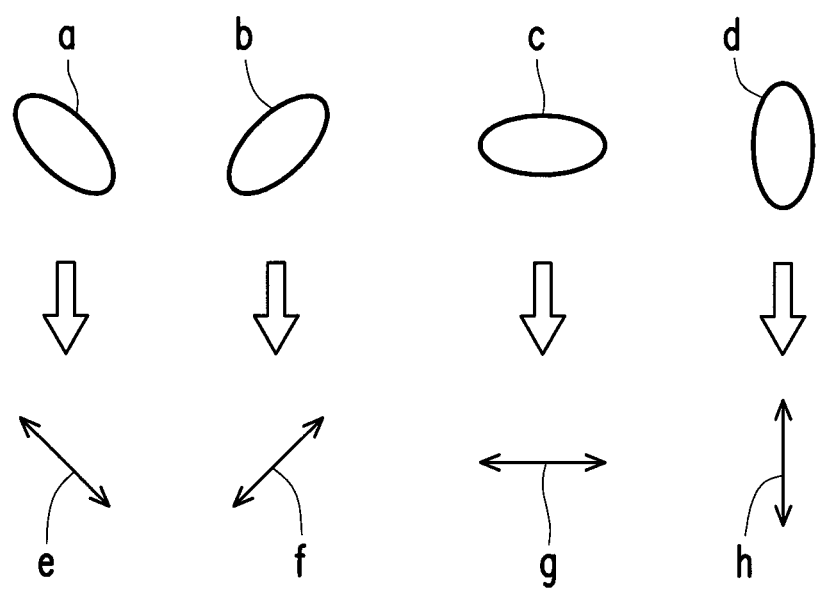
FIG. 6 is a schematic diagram of corresponding relationships between ellipse shapes and sight directions according to an embodiment of the invention.

Then, in step S320, the image analysis module 140 determines a sight direction according to the ellipse feature. For example, the sight determination module 211 inquires the database 150 according to the obtained ellipse feature, and obtains the corresponding sight direction according to the predetermined ellipse equation complying with the ellipse feature. For example, FIG. 6 is a schematic diagram of corresponding relationships between ellipse shapes and sight directions according to an embodiment of the invention. In FIG. 6, only the ellipse shapes corresponding to four predetermined ellipse equations are illustrated, and each of the ellipse shapes has the corresponding sight direction. As shown in FIG. 6, an ellipse shape a corresponds to a left up right down sight direction e, an ellipse shape b corresponds to a right up left down sight direction f, an ellipse shape c corresponds to a horizontal sight direction g, and an ellipse shape d corresponds to a vertical sight direction h. However, the invention is not limited thereto. The corresponding ellipse shape is obtained according to the predetermined ellipse equation complying with the ellipse feature, so as to obtain the corresponding sight direction.

After the sight direction is obtained, the sight determination module 211 further calculates a pupil displacement, and obtains a displacement direction and a displacement of a sight point according to the sight direction and the pupil displacement, so as to move a cursor in a screen. For example, displacement of the pupil central points in two tandem pupil images is calculated.

Here, the processing unit 110 first converts an initial pupil position into screen cursor coordinates according to a coordinate system conversion method. For example, a perspective transformation method is used to generate a coordinate conversion matrix, and the coordinate conversion matrix is configured to convert the pupil position of the eye image into the screen cursor position. Then, the cursor on the screen is moved according to the sight direction and the pupil displacement obtained according to the subsequently received original image.

The present invention further provides a computer program product adapted to the pupil positioning apparatus. The computer program product is basically composed of a plurality of program instructions (for example, an organization chart establishing program instruction, a table approving program instruction, a setting program instruction, and a deployment program instruction, etc), and these program instructions are loaded into the pupil positioning apparatus and executed by the same to accomplish various steps of the method for positioning pupil and various functions of the pupil positioning apparatus described above.

In summary, by analysing the curve segments and the curvatures thereof included in the pupil contour, the ellipse shape corresponding to the pupil contour is obtained. In this way, the sight direction of the pupil and the pupil displacement can be quickly and accurately determined, so as to accurately detect the pupil position to implement accurate eye tracking and achieve diversified application.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A method for positioning pupil, comprising:
    obtaining a pupil image;
    obtaining a pupil contour from the pupil image;
    calculating curvatures of a plurality of curves in the pupil contour from a start point of the pupil contour along a predetermined direction to obtain curvature information, wherein the curvature information comprises curvatures in one or more of curve segments;
    obtaining an ellipse feature according to the curvature information of the pupil contour, wherein the curvature of each curve in the pupil contour is complied with a same curvature equation;
    obtaining an ellipse shape corresponding to the ellipse feature;
    determining a sight direction according to the ellipse shape so as to obtain a displacement direction of a sight point, wherein the ellipse shape comprises a first axis and a second axis, the sight direction parallel to the first axis, and the first axis is longer than the second axis;
    calculating a pupil displacement according to a first pupil central point of the pupil image and a second pupil central point of previous pupil image, so as to obtain a displacement of the sight point; and
    converting an initial pupil position into a screen cursor coordinates, and moving a cursor on a screen according to the displacement direction of the sight point and the displacement of the sight point.

2. The method for positioning pupil as claimed in claim 1, wherein the step of obtaining the ellipse feature according to the curvature information of the pupil contour comprises:
    determining whether the curvature of each curve is complied with the same curvature equation within an error tolerance range;
    setting the curves complied with the same curvature equation within the error tolerance range as a same curve segment; and
    obtaining the ellipse feature according to the one or more curve segments obtained based on the pupil contour.

3. The method for positioning pupil as claimed in claim 2, wherein the step of obtaining the ellipse feature according to the curvature information of the pupil contour comprises:
    filtering the one or more curve segments that are not complied with a predetermined curving direction.

4. The method for positioning pupil as claimed in claim 1, wherein the step of determining the sight direction according to the ellipse feature comprises:
    inquiring the sight direction corresponding to the ellipse feature from a database.

5. The method for positioning pupil as claimed in claim 1, further comprising:
    receiving an original image;
    extracting a face image from the original image;
    detecting a nostril area of the face image to obtain nostril position information;
    obtaining an eye image based on the nostril position information; and
    obtaining the pupil image from the eye image.

6. The method for positioning pupil as claimed in claim 5, wherein the step of obtaining the eye image according to the nostril location information comprises:
    estimating a central point and a length and a width of an eye search frame according to a distance between a first nostril central point and a second nostril central point in the nostril position information, so as to obtain the eye image from the eye search frame.

7. A pupil positioning apparatus, comprising:
    an image capturing unit for obtaining an original image;
    a storage unit having an image analysis module; and
    a processing unit coupled to the image capturing unit and the storage unit, wherein the processing unit activates the image analysis module to obtain a pupil image from the original image, obtain a pupil contour from the pupil image, calculate curvatures of a plurality of curves in the pupil contour from a start point of the pupil contour along a predetermined direction to obtain curvature information comprising curvatures in one or more of curve segments, obtain an ellipse feature according to the curvature information of the pupil contour, obtain an ellipse shape corresponding to the ellipse feature, determine a sight direction according to the ellipse shape so as to obtain a displacement direction of a sight point, calculate a pupil displacement according to a first pupil central point of the pupil image and a second pupil central point of previous pupil image to obtain a displacement of the sight point, and convert an initial pupil position into a screen cursor coordinates, and move a cursor on a screen according to the displacement direction of the sight point and the displacement of the sight point,
    wherein the curvature of each curve in the pupil contour is complied with a same curvature equation,
    wherein the ellipse shape comprises a first axis and a second axis, the sight direction parallel to the first axis, and the first axis is longer than the second axis.

8. The pupil positioning apparatus as claimed in claim 7, wherein the image analysis module comprises:
- a pupil detection module for detecting the pupil image from an eye image, and obtaining the pupil contour from the pupil image, wherein the eye image is obtained from the original image;
- a curvature calculation module for calculating the curvature information of the pupil contour, so as to obtain the ellipse feature; and
- a sight determination module for determining the sight direction according to the ellipse feature.

9. The pupil positioning apparatus as claimed in claim 8, wherein the curvature calculation module calculates the curvatures of the one or more curve segments in the pupil contour,
- the curvature calculation module calculates the curvatures of the pupil contour at the plurality of curves from the start point of the pupil contour along the predetermined direction, and within an error tolerance range, determines whether the curvature of each curve is complied with the same curvature equation; the curvature calculation module sets a plurality of continuous curves complied with the same curvature equation within the error tolerance range as a same curve segment, and obtains the ellipse feature according to the one or more curve segments obtained based on the pupil contour.

10. The pupil positioning apparatus as claimed in claim 9, wherein the curvature calculation module filters the one or more curve segments that are not complied with a predetermined curving direction.

11. The pupil positioning apparatus as claimed in claim 8, wherein the storage unit further comprises:
- a database for storing a plurality of predetermined ellipse features and the corresponding sight directions,
- wherein the sight determination module inquiring the database, and obtains the corresponding sight direction according to one of the predetermined ellipse features complying with the ellipse feature.

12. The pupil positioning apparatus as claimed in claim 8, wherein the sight determination module further calculates the pupil displacement to obtain the displacement of the sight point.

13. The pupil positioning apparatus as claimed in claim 8, wherein the image analysis module further comprises:
- a face detection module for extracting a face image from the original image;
- a nostril detection module for detecting a nostril area of the face image to obtain nostril position information; and
- an eye detection module for obtaining the eye image based on the nostril position information.

14. The pupil positioning apparatus as claimed in claim 13, wherein the eye detection module estimates a central point and a length and a width of an eye search frame according to a distance between a first nostril central point and a second nostril central point in the nostril position information, so as to obtain the eye image from the eye search frame.

15. A non-transitory computer program product, adapted to a pupil positioning apparatus, wherein when the pupil positioning apparatus loads and executes a computer program of the computer program product, the method for positioning pupil as claimed in claim 1 is implemented.

* * * * *